United States Patent [19]

Adinolfi

[11] Patent Number: 5,159,739
[45] Date of Patent: Nov. 3, 1992

[54] SANITARY EQUIPMENT HANDLER HAVING MAGNETICALLY HELD, DETACHABLE HANDLE

[76] Inventor: Raphael A. Adinolfi, 515 - 72 St., Brooklyn, N.Y. 11209

[21] Appl. No.: 720,363

[22] Filed: Jun. 25, 1991

[51] Int. Cl.⁵ .................. A47B 95/02; E05B 47/00
[52] U.S. Cl. ................................ 16/114 R; 16/124; 16/DIG. 24; 294/65.5; 312/348.6
[58] Field of Search ............ 16/114 R, 124, DIG. 24; 312/320; 294/65.5

[56] References Cited

U.S. PATENT DOCUMENTS

| | | | |
|---|---|---|---|
| 2,440,170 | 4/1948 | Duefrene | 16/114 R |
| 2,976,075 | 3/1961 | Budreck | 294/65.5 |
| 3,302,566 | 2/1967 | Blanchet | 16/114 R |
| 3,646,492 | 2/1972 | Westermann | 294/65.5 |
| 4,181,340 | 1/1980 | Kofford | 294/65.5 |
| 5,086,523 | 2/1992 | De Mott et al. | 16/114 R |

*Primary Examiner*—John Sipos
*Assistant Examiner*—Carmine Cuda

[57] ABSTRACT

A device to allow health practitioners' cabinet drawers to be opened and operating lights and other movable operating equipment to be repositioned as he works, without the need to grasp, and thereby contaminate, the existing handles. The device comprises magnet devices attached to the drawers and equipment and a hand-held sterilizable element for contacting the attached magnet devices and moving the drawers and equipment, thus allowing for one easily washable and sterilizable handle to be used for any individual patient.

5 Claims, 1 Drawing Sheet

SANITARY EQUIPMENT HANDLER HAVING MAGNETICALLY HELD, DETACHABLE HANDLE

BACKGROUND OF THE INVENTION

1. Field of the Invention

The invention relates generally to magnetic bars, attached to the handles of health practitioners' equipment and cabinet drawers, that when contacted by a magnet-affected metal handle, will permit repositioning of the said equipment and opening of drawers. Then, when treatment is complete on a patient, sterilization of that handle by any means can be achieved.

2. Description of the Prior Art

Heretofore, in a dental operatory, many pieces of equipment and furniture that are handled or touched during each procedure must be disinfected after each patient. This can be very time-consuming because the hands, whether gloved or ungloved, are involved in contact with the patients' body fluids, including saliva and blood. This invention would eliminate the need for disinfection of the many such items as cabinet drawer handles, the operating light, and other movable operating equipment because they would no longer have to be gripped by contaminating fingers. Now only one easily removable item needs to be sterilized.

SUMMARY OF THE INVENTION

The invention relates to a device to allow health practitioners' cabinet drawers to be opened and operating lights and the other movable operating equipment to be repositioned as he works, using only one handle. It comprises a means for magnetically engaging various items and moving them with the same one handle while working on any one given patient.

It is comprised of a magnetic bar embedded in plastic, which attaches to items that are to be manipulated. Secondly, it is comprised of a metal handle that is affected by magnetism.

It is an object of the invention to provide a device, which is a supplementary handle, for manipulating operatory drawers, lights, and other movable equipment during procedures. This can now be done without touching, and contaminating the existing handles, thereby decreasing the amount of time needed to disinfect the equipment between patients.

DESCRIPTION OF THE PREFERRED EMBODIMENT

Figure 1:
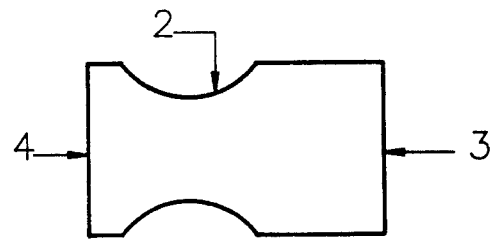
FIG. 1 is a side view showing the hand-held element of the Sanitary Equipment Handler.
Figure 2:
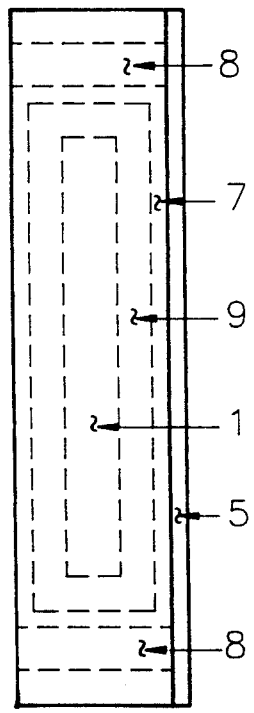
FIG. 2 is a top view showing the magnetic handling attachment of the Sanitary Equipment Handler.

Referring to FIGS. 1, 2, 3, and 4, an embodiment of the Sanitary Equipment Handler is shown. In this embodiment, a magnet 1, embedded in an encasement 7 and a hand-held element 6 are shown. The magnet 1 is embedded in an encasement 7 and is encompassed on two sides by steel pole pieces 9, placed so as to position the magnetic field for maximum attaching effect. The encasement 7 may be constructed of any material and the invention relates to any configuration of the encasement 7. The encasement 7, containing the magnet 1 and the pole pieces 9, is attached to cabinetry and other movable operating equipment in a health practitioners' operatory. Any means for attaching the magnetic handling attachment to the equipment may be used, including self-adhesive backing 5, hardware placed through holes 8 provided, or other means.

Figure 4:
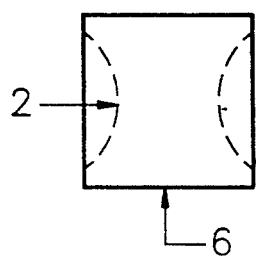
FIG. 4 is a front view showing the hand-held element of the Sanitary Equipment Handler.

Referring to FIGS. 1 and 4, a representation of the hand-held element 6 is shown. This piece may be made of any material or combination of materials that can be affected strongly by a magnet, including, but not limited to magnet-affectable stainless steel. In this embodiment, finger grips 2 are provided a sufficient distance away from the magnet-contacting surface 3, so that soiled fingers will not contact the cabinet drawers or the magnet housing device against which it will be placed. It is held by fingers in depressions 2 and the front surface 4 rests in the hand.

Figure 3:
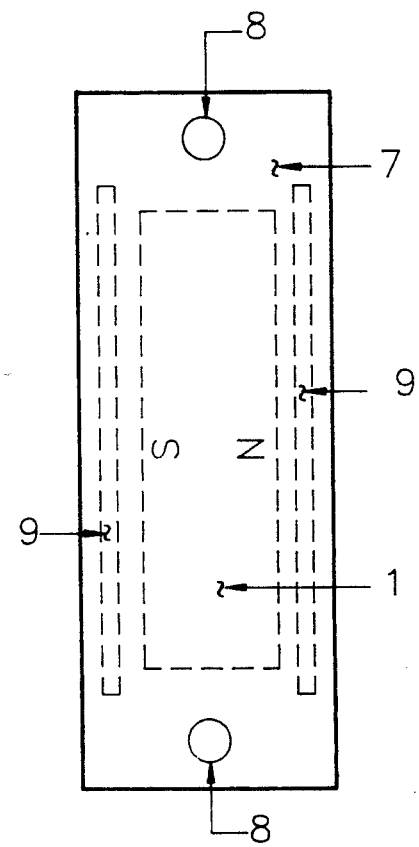
FIG. 3 is a plan view showing the magnetic handling attachment of the Sanitary Equipment Handler.

The handling attachment shown in FIG. 3 is attached to cabinet drawers, the operating light, or other movable operating equipment. To open a drawer or reposition equipment during a procedure, the health practitioner picks up the hand-held element 6 and places it on the magnet housing device. The drawers and other equipment may then be moved without touching the existing handles, and thereby contaminating them with the fingers. After treating that one patient, the one hand-held device can then be cleaned and placed in the sterilizer to prepare it for use with a different patient. The invention minimizes the standard practice of having to disinfect, after each patient, all drawer handles and handles of all equipment.

Although one detailed embodiment of the invention is illustrated in the drawings and previously described in detail, the invention contemplates any configuration, design, and relationship of components which will function in a similar manner and which will provide the equivalent result.

I claim:

1. A device for opening cabinet drawers and repositioning operating equipment without touching and thereby contaminating the existing handles, which comprises:
   (a) a plurality of magnet means, each magnet means comprising a magnet embedded in an encasement, and which are attached to said cabinet drawers and to the handles of said other movable operating equipment; and
   (b) a sterilizable element which is held in the hand, for contacting said magnet means for opening said drawers and moving said equipment; said magnet means having a sufficient attracting force on said sterilizable element to move said drawers and said equipment; said sterilizable element having a substantially planar contact surface for contacting and readily attaching to a substantially planar contact surface of the magnet means within a range of positions along said magnet means contact surface.

2. A sanitary equipment handler as recited in claim 1, in which the magnet is encompassed on two sides by steel pole pieces, placed so as to position the magnetic field for maximum attaching effect.

3. A sanitary equipment handler as recited in claim 2, in which each of said magnetic means has a means for attachment to cabinetry and to the handles of movable operating equipment.

4. A sanitary equipment handler as recited in claim 3, in which the hand-held element is easily washable and sterilizable by any means.

5. A sanitary equipment handler as recited in claim 4, in which the magnetic means is made of a material which will provide it with a smooth, disinfectable surface.

* * * * *